(12) United States Patent
Chong et al.

(10) Patent No.: US 6,953,540 B2
(45) Date of Patent: Oct. 11, 2005

(54) CONTINUOUS PROCESS FOR THE PREPARATION OF ENCAPSULATED CYCLOPROPENES

(75) Inventors: Joshua Anthony Chong, Lansdale, PA (US); Vincent John Farozic, Blue Bell, PA (US); Richard Martin Jacobson, Chalfont, PA (US); Bret Alan Snyder, Wilmington, DE (US); Randall Wayne Stephens, Perkasie, PA (US); David Wayne Mosley, Arlington, MA (US)

(73) Assignee: Rohm and Haas Company, Philadelphia, PA (US)

( * ) Notice: Subject to any disclaimer, the term of this patent is extended or adjusted under 35 U.S.C. 154(b) by 365 days.

(21) Appl. No.: 09/951,049

(22) Filed: Sep. 12, 2001

(65) Prior Publication Data

US 2002/0043730 A1 Apr. 18, 2002

Related U.S. Application Data

(60) Provisional application No. 60/236,657, filed on Sep. 29, 2000.

(51) Int. Cl.[7] .................................................. B01J 13/02
(52) U.S. Cl. .................. 264/4.3; 264/4.1; 264/4.33; 264/4.4; 528/367; 528/369; 528/392; 528/397; 528/422; 528/499; 528/502; 528/503

(58) Field of Search .................... 264/4.1, 4.3, 4.33, 264/4.4; 528/367, 369, 392, 397, 422, 499, 502, 503

(56) References Cited

U.S. PATENT DOCUMENTS

| | | | |
|---|---|---|---|
| 5,518,998 A | 5/1996 | Bäckström et al. | ............ 514/3 |
| 5,723,714 A | 3/1998 | Binger | ....................... 585/638 |
| 6,017,849 A | 1/2000 | Daly et al. | .................. 504/114 |

FOREIGN PATENT DOCUMENTS

DE    4333491 A1    4/1995

OTHER PUBLICATIONS

An Efficient and Convenient Synthesis of 1–Methylcyclopropene. J. Org. Chem, vol. 36, No. 9, 1971, pp. 1320–1321.
Cyclopropene: A New Simple Synthesis and Diels–Alder Reactions with Cyclopentadiene and 1,3–Diphenylisobenzofuran. J. Org. Chem 1996, 61, pp. 6462–6464.
Methylenecyclopropane and 1–and 3–Methylcyclopropene from Methallyl Chlorides and Alkali Amides (A translation of the German Reference). Liebigs Ann. Chem. 1973, pp. 1219–1235.

*Primary Examiner*—Samuel A. Acquah
(74) *Attorney, Agent, or Firm*—Thomas Rogerson

(57) ABSTRACT

The present invention relates to a continuous method to prepare encapsulated cyclopropenes, a method to purify cyclopropene gas, and a method to prepare an α-cyclodextrin/cyclopropene complex.

1 Claim, No Drawings

CONTINUOUS PROCESS FOR THE PREPARATION OF ENCAPSULATED CYCLOPROPENES

CROSS REFERENCE TO RELATED PATENT APPLICATIONS

This is a non-provisional application of prior U.S. provisional application Ser. No. 60/236,657 filed Sep. 29, 2000.

The present invention relates to a continuous method to prepare encapsulated cyclopropenes, a method to purify cyclopropene gas, and a method to prepare an α-cyclodextrin/cyclopropene complex.

Cyclopropenes have a variety of uses in the chemical industry. One recent discovery is the ability of 1-methylcyclopropene, and related analogs, to inhibit the action of ethylene on plants (see U.S. Pat. No. 5,518,988). Several syntheses of cyclopropene and its simple derivatives have been reported. The most widely practiced process is the sodium amide induced α-elimination of an allylic chloride (see F. Fisher and D. Applequist, *J. Org. Chem.*, 30, 2089 (1965)). Similar synthesis methods are disclosed in U.S. Pat. No. 6,017,849.

Unfortunately, 1-methylcyclopropene and its analogs are relatively unstable due to their potential for undergoing oxidation, "ene", and other reactions. There is a particular stability problem of these compounds resulting in an explosive hazard when the compound is warmed in the liquid state. To solve such problems, the inventors of U.S. Pat. No. 6,017,849 developed a method of incorporating these compounds in a molecular encapsulation agent complex in order to stabilize their reactivity and thereby provide a convenient and safe means of storing, transporting, applying, and delivering the active compounds to plants. The encapsulating agents include cyclodextrins, crown ethers, polyoxyalkylenes, polysiloxanes, zeolites, and others.

A difficulty in preparing encapsulated cyclopropenes is that known processes, including processes disclosed in U.S. Pat. No. 6,017,849, employ batch methods. This results in long processing times, principally related to the fact that as the cyclopropene complexes with the encapsulation agent the partial pressure of the cyclopropene declines over time. As the partial pressure declines, the rate of encapsulation also declines. A second difficulty related to batch processes is that the encapsulating agent is typically suspended or dissolved in a solvent. After the cyclopropene complex forms there is competition between the solvent and the cyclopropene in the encapsulation agent which results in desorption of a portion of the encapsulated cyclopropene.

We have discovered a process in which cyclopropenes can be encapsulated in a continuous manner which avoids the above-noted difficulties. One requirement of this process is that the encapsulating agent be soluble in a solvent in the absence of the cyclopropene but when the cyclopropene is encapsulated the complex precipitates from the solvent. Another advantage of the present invention is that the amount of selective inclusion of the gaseous active compounds such as cyclopropene and methylcyclopropene into the molecular encapsulation agent far exceeds the amount expected using the reported batch preparation processes.

While it is well documented in U.S. Pat. No. 5,518,988 that methylcyclopropene, and other similar compounds, are active in blocking the action of ethylene on plants, it has been discovered that not all methods of synthesis are as effective or preferable as the presently claimed method of preparation. First, it is necessary to avoid producing products (or impurities) that reversibly bind to the same ethylene receptor site as the intended active compound. Because these impurities do not irreversibly bind in a manner consistent with the inactivation of the receptor site, the effectiveness of using such a reaction product mixture without further processing is reduced. The specific impurities that must be avoided in the synthesis in order to obtain optimal performance of the reaction mixture include methylenecyclopropane, methylcyclopropanes, butenes, and butanes.

Although the reported reactions work reasonably well, methods which improve the isomer ratio (that is, for example, increased 1-methylcyclopropene compared to methylenecyclopropane) often do so at the expense of overall product yield (see Koster, et. al., *Liebigs Ann. Chem.*, 1219 (1973). Because of these problems, there is still a need for a method to prepare encapsulated cyclopropenes in high yield and in high isomer purity. We have discovered a continuous process for the preparation of such encapsulated cyclopropenes which provides the product in high yield and which contains high quantities of the cyclopropene per unit of product.

The present invention, therefore, is a method to prepare encapsulated cyclopropenes, comprising the steps of:
a) contacting a first stream comprising an allyl compound of formula I:

wherein:
X is a leaving group; and
R is hydrogen or a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy;
with a second stream comprising a base comprising a non-nucleophilic strong base, optionally comprising a weaker base;
and an inert solvent, in a first vessel, causing evolution of a cyclopropene of formula II as a gas;

b) passing the cyclopropene gas through a condenser held at a temperature less than the boiling point of the allyl compound and greater than the boiling point of the cyclopropene;
c) contacting the cyclopropene gas with a solution of the encapsulation agent in a second vessel to give a precipitate of the encapsulated cyclopropene;
d) separating the precipitate from the solution,
e) optionally washing the precipitate; and
f) drying the precipitate.

As used herein, the term "alkyl" means both straight and branched chain ($C_1$–$C_{20}$) radicals which include, for example, methyl, ethyl, n-propyl, isopropyl, 1-ethylpropyl, n-butyl, tert-butyl, isobutyl, 2,2-dimethylpropyl, pentyl, octyl, and decyl. The terms "alkenyl" and "alkynyl" mean ($C_3$–$C_{20}$)alkenyl and ($C_3$–$C_{20}$)alkynyl groups such as, for example, 2-propenyl, 2-butenyl, 3-butenyl, 2-methyl-2- propenyl, and 2-propynyl. The term "cycloalkylalkyl" means a ($C_1$–$C_{15}$)alkyl group substituted with a ($C_3$–$C_6$) cycloalkyl group such as, for example cyclopropylmethyl, cyclopropylethyl, cyclobutylmethyl, and cyclopentylethyl. The term "haloalkyl" means an alkyl radical wherein one or more of the hydrogen atoms have been replaced by a halogen atom. The term "halogen" means fluorine, chlorine, bromine, and iodine. The term "strong base" means a non-nucleophilic base with a $pK_a$ greater than 35. The term "inert solvent" means a solvent which does not react with the strong base, the weaker base, the allyl halide, or the resulting cyclopropene.

As used herein, all percentages are percent by weight and all parts are parts by weight, unless otherwise specified and are inclusive and combinable. All ratios are by weight and all ratio ranges are inclusive and combinable. All molar ranges are inclusive and combinable.

Preferably, X is a leaving group selected from halogen, alkyl or aryl sulfonyloxy, alkyl or aryl sulfate, and alkoxy. More preferably, X is chloro, bromo, iodo, benzenesulfonyloxy, p-toluenesulfonyloxy, methanesulfonyloxy, or t-butoxy. Even more preferably, X is chloro, bromo, or benzenesulfonyloxy. Most preferably, X is chloro or bromo.

Preferably, R is ($C_1$–$C_{10}$)alkyl. More preferably, R is ($C_1$–$C_8$)alkyl. Even more preferably R is ($C_1$–$C_4$)alkyl. Most preferably, R is methyl.

Preferably, the inert solvent is a hydrophobic, nonpolar solvent. More preferably, the inert solvent is an aliphatic or aromatic hydrocarbon such as, for example, mineral oil, benzene, toluene, or xylene; an ether such as, for example, diethyl ether, tetrahydrofuran, or dioxane, a halogenated hydrocarbon such as, for example a perhaloalkane, liquid ammonia, or lower alkyl amine or lower dialkyl amine such as, for example, methylamine or dimethylamine. Even more preferably, the solvent is an aliphatic or aromatic hydrocarbon. Most preferably, the solvent is mineral oil. Preferably, the solvent has a boiling point greater than 100° C. The solvent may be a mixture of more than one inert solvent.

Preferably, the strong base is an alkali metal salt of an amine or an organometallic base. More preferably, the strong base is sodium amide, potassium amide, lithium amide, or phenyllithium. Most preferably, the strong base is sodium amide. The strong base may be a mixture of more than one strong base.

Preferably, the base further comprises a mixture of the strong base and a weaker base. As used herein, the term "weaker base" means a non-nucleophilic base with a $pK_a$ of from 26 to 35, or the conjugate acid thereof. The amount of strong base used in the method will vary depending upon the weaker base used, the inert solvent, and the temperature at which the reaction is conducted. Preferably, the amount of strong base used is from 0.1 to 20 moles per mole of allyl compound of formula I. More preferably the amount of strong base used is from 0.5 to 2 moles per mole of allyl compound of formula I. Most preferably, the amount of strong base used is from 0.7 to 1.4 moles per mole of allyl compound of formula I.

Preferably, the weaker base is soluble in the inert solvent. More preferably, the weaker base is a silyl amine, a disilazane, their cyclic analogs, mixed cyclic silazane/ether analogs, or metal salts thereof. Even more preferably, the weaker base is a silyl amine or a disilazane. Still more preferably, the weaker base is a dialkyl- or trialkyl, diaryl- or triaryl, or mixed alkyl/aryl silyl amine; a tetraalkyl-, pentaalkyl- or hexaalkyl, tetraaryl-, pentaaryl-, or hexaaryl, or mixed alkyl/aryl disilazane; or their cyclic analogs. Still more preferably, the weaker base is 1,1,1-triphenylsilylamine, tri-n-hexylsilylamine, 1,1,1,3,3,3-hexamethyldisilazane, 1,1,3,3-tetramethyldisilazane, 2,2,4,4,6,6-hexamethylcyclotrisilazane, octamethylcyclotetrasilazane, hexaethyldisilazane, 1,3-di-n-octyltetramethyldisilazane, or 2,2,5,5-tetramethyl-2,5-disila-1-azacyclopentane. Most preferably, the weaker base is 1,1,1,3,3,3-hexamethyldisilazane. The weaker base can be a mixture of more than one weaker base. The amount of weaker based used in the method of this invention will vary depending upon the strong based used, the inert solvent used, and the temperature at which the reaction is conducted. Preferably, the amount of weaker base used is from 0.001 to 0.95 moles per mole of strong base used. More preferably, the amount of weaker base used is from 0.005 to 0.4 moles per mole of strong base. Most preferably, the amount of weaker base used is from 0.01 to 0.2 moles per mole of strong base.

The order of addition of the first and second streams to the solvent is not critical. Preferably, the first and second streams are added concurrently to the first vessel. More preferably the addition is on a mole to mole (allyl compound to strong base) basis. Most preferably, the second stream further comprises the inert solvent. The addition of the allyl compound to the base at a near 1:1 ratio helps ensure that the cyclopropene produced is not exposed to excess base for a significant period of time before distilling from the solvent mixture. This helps prevent formation of unwanted isomers and side products.

The temperature at which the method of this invention is carried out is not critical but may affect the reaction rate. However, because cyclopropenes are reactive compounds, care must be taken to ensure that the temperature is kept below that at which decomposition or side reactions occur but is high enough such that the cyclopropene produced distills as it is being produced from the reaction mixture in the first vessel. As a safety precaution, it is useful to ensure that the cyclopropene produced in the first vessel does not condense anywhere in the processing equipment.

Preferably, the reaction mixture is stirred or otherwise agitated and/or sparged or purged with an inert gas during the reaction. Preferably the inert gas is nitrogen. More preferably, the agitation rate is sufficiently high to ensure that the cyclopropene distills from the reaction mixture as soon as possible after being formed. Fast removal of the cyclopropene from the reaction mixture has been found to reduce production of side products such as alkylidenecyclopropanes and teleomers. A portion of the spent contents of the first vessel is preferably removed as fresh first and second streams are added to the vessel to promote continuous operation of the process in the first vessel.

The pressure at which the reaction is conducted is also not critical. However, because the rate of complexation with the encapsulating agent in step c) increases with increasing gas pressure, maintaining a consistently high pressure improves the overall yield of the encapsulated cyclopropene. Thus, instead of using a batch shaking method for contacting the cyclopropene gas and the encapsulating agent, wherein the pressure of cyclopropene gas declines as it complexes, the method of the present invention continuously supplies the cyclopropene gas to the encapsulating agent in order to maintain approximately 1 atmosphere of pressure at all times. Use of cyclopropene gas pressures higher than 1 atmosphere are expected to further accelerate the encapsulation rate. However, two safety concerns occur at higher pressures: the uncertain stability of cyclopropene gas to explosive decomposition above 1 atmosphere and the fact that the gas will condense at higher temperatures when its pressure is above 1 atmosphere (at 25° C., for instance, calculation suggests 1-methylcyclopropene will condense at approximately 2.5 atmospheres). Preferably, the pressure will be from 0.9 atmosphere to 1.5 atmospheres. More preferably, the pressure will be from 1.0 atmosphere to 1.1 atmospheres. Most preferably, the pressure will be 1.0 atmosphere, that is, ambient pressure. However, pressure or vacuum may be utilized to affect the relative boiling points of the cyclopropene produced, the starting allyl compound, and the inert solvent to aid in separation of the cyclopropene from the reaction mixture.

The condenser used to preferentially condense the allyl compound preferably returns the condensate directly into the first vessel. The condenser temperature, when the cyclopropene is 1-methylcyclopropene, is preferably held at from 10° C. to 20° C.; more preferably from 10° C. to 15° C.; most preferably 15° C.

Another embodiment of the present invention includes the step of purifying the cyclopropene gas prior to step c) by passing the cyclopropene gas stream produced in the first vessel through one or more gas scrubbers. Such scrubber(s) incorporate a liquid which, when in contact with the cyclopropene gas stream, removes undesirable components. Such components include, for example, ammonia (when the strong base is a metal amide), unreacted allyl compound of formula I, and other gaseous impurities. Preferably, the scrubbers comprise two scrubbers, one in which only water is used as the liquid (a water scrubber), and one in which the liquid is an aqueous solution of components which react with gaseous impurities in the cyclopropene gas stream (a reactive scrubber). When the scrubbers comprise two scrubbers (a first scrubber and a second scrubber) they can be arranged in any order. However, the preferred order is for the cyclopropene gas stream to pass through the water scrubber first and the reactive scrubber second. The scrubbers may be any apparatus which provides contact between the cyclopropene gas stream and the liquid. Such scrubbers range from the simple, for example, a dip tube extending into a flask containing the liquid, to the complex, for example, countercurrent scrubbers. Both scrubbers are preferably countercurrent scrubbers. In each case, the cyclopropene gas stream preferably enters the scrubber at the bottom and exits at the top. Because the water scrubber is intended to remove water soluble gasses the liquid used is preferably water alone. The reactive scrubber is primarily intended to remove residual allyl compound and, as a result, the liquid is preferably a reactive solvent mixture comprising compounds which will react with the allyl compound. More preferably, the reactive solvent mixture will react with the allyl compound to give compounds which are less volatile and/or less toxic than the allyl compound. Preferably, the reactive solvent comprises a thiol. More preferably, the reactive solvent comprises an aqueous solution of an alcohol, an amine, and a thiol. Most preferably the reactive solvent comprises 30 to 50% water, 30 to 50% of an alcohol, 5 to 20% of an amine, and 5 to 20% of a thiol. Preferably, the alcohol is iso-propanol, the amine is ethanolamine, and the thiol is 2-mercaptoethanol. Most preferably, the reactive solvent comprises 50% water, 30% iso-propanol, 10% ethanolamine, and 10% 2-mercaptoethanol. Preferably the reactive solvent, or a portion of the reactive solvent, is recycled through the scrubber. Fresh reactive solvent may be added to the recycled reactive solvent to maintain appropriate volume and flow rates through the scrubber.

After exiting from the one or more gas scrubbers, the purified cyclopropene gas is contacted with a solution of the encapsulating agent in a second vessel forming a cyclopropene/encapsulating agent precipitate. This complex is continuously separated from the solution, which then may be recycled or discarded. Preferably, the cyclopropene gas, the encapsulating agent, and water are continuously fed into the second vessel, in separate or combined streams, and a steady take-off of the precipitate, water, and any remaining solute occurs. This is an improvement over the batch method disclosed in U.S. Pat. No. 6,017,849 because it allows greater quantities of product to be complexed in smaller volume equipment and without labor-intensive charging and discharging of the vessels. Furthermore, scale-up and scale-down of the process is made easier. This invention further allows for recycle loops and other enhancements resulting in increased purity and/or yield of the reaction product.

Preferred encapsulating agents include cyclodextrins, crown ethers, polyoxyalkylenes, and polysiloxanes. More preferred encapsulating agents include alpha-cyclodextrin, beta-cyclodextrin, and gamma-cyclodextrin. The most preferred encapsulating agent, particularly when the cyclopropene is 1-methylcyclopropene, is alpha-cyclodextrin. However, as one skilled in the art will appreciate, any cyclodextrin or mixture of cyclodextrins, cyclodextrin polymers, as well as modified cyclodextrins can also be utilized pursuant to the present invention. Cyclodextrins are available from Wacker Biochem Inc., Adrian, Mich. or Cerestar USA, Hammond, Ind., as well as other vendors.

Once the precipitate is formed in an aqueous environment, reduction of the cyclopropene gas pressure shifts the equilibrium toward decomplexation and subsequent release of the cyclopropene gas from the complex. In order to maintain a high yield of solid, precipitated complex, the complex must be rapidly brought to a dry state. That is, rapid dewatering of the precipitated is preferred. We have found that slow drying reduces the cyclopropene gas content of the final, isolated complex. The method of U.S. Pat. No. 6,017,849 uses filter bags followed by inefficient free convection drying in a room under ambient conditions of temperature and humidity to provide a product containing from 0.1 to 0.5 percent cyclopropene gas, by weight. To achieve rapid dewatering, a continuous belt filter is preferred. Using such a filter, a thin wetcake is formed, which may be washed with one or more solvents. Preferred wash solvents include, for example, a water-solubilizing solvent that evaporates faster than water alone. Preferred solvents include, for example, methanol, ethanol, isopropanol, methyl formate, methyl acetate, and acetone. Such solvents may also be used in mixtures or sequentially in any order. To further dry the precipitate, heated air or nitrogen (30° C. to 150° C.) may be passed through the wet cake. Preferably, the air or nitrogen is heated to approximately 80° C. Moisture content of the resulting dry cake is preferably less than 10% by weight; more preferably less than 8% by weight. Using such equipment and processes, the cyclopropene content in the final product is typically from 2.0 to 5.0 percent, by weight when the cyclopropene is 1-methylcyclopropene. Cyclopropenes with higher molecular weights will result in complexes with a higher percentage by weight of the cyclopropene. Other equipment and processes which may be equally applicable to achieve rapid dewatering include, for example, centrifugation, spray drying, fluid bed drying, and rotary drum filtration. Other drying equipment and processes will be obvious to those skilled in the art.

One preferred embodiment of the present invention is, therefore, a method to prepare encapsulated cyclopropenes, comprising the steps of:

a) contacting a first stream comprising an allyl compound of formula I:

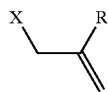

wherein:
X is a leaving group; and
R is hydrogen or a substituted or unsubstituted alkyl, alkenyl, alkynyl, cycloalkyl, cycloalkylalkyl, phenyl, or naphthyl group;
wherein the substituents are independently halogen, alkoxy, or substituted or unsubstituted phenoxy;
with a second stream comprising a base comprising:
i) a non-nucleophilic strong base or
ii) a mixture of a non-nucleophilic strong base and a weaker base;
and an inert solvent, in a first vessel, causing evolution of a cyclopropene of formula II as a gas;

b) passing the cyclopropene gas through a condenser held at a temperature less than the boiling point of the allyl compound and greater than the boiling point of the cyclopropene;
c) returning the condensed allyl compound into the first vessel;
d) scrubbing the cyclopropene gas in a first scrubber with water to remove water soluble impurities;
e) scrubbing the cyclopropene gas in a second scrubber with a reactive solvent mixture to remove residual allyl compound to give purified cyclopropene gas;
e) contacting the purified cyclopropene gas with a solution of the encapsulation agent in a second vessel to give a precipitate of the encapsulated cyclopropene;
f) separating the precipitate from the solution,
g) optionally washing the precipitate; and
h) rapidly drying the precipitate.

In addition to being applicable to the continuous process of this invention, several of the individual steps of the process provide improved results when used alone in batch processes for production of a cyclopropene gas, purification of a cyclopropene gas, and encapsulation of a cyclopropene gas. Therefore, another embodiment of the present invention is an improved method for the preparation of cyclopropene gas, comprising contacting a first stream comprising an allyl compound of formula I:

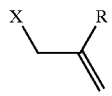

wherein:
X is a leaving group; and
R is hydrogen or a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy;
with a second stream comprising a base comprising a non-nucleophilic strong base, optionally containing a weaker base;
and an inert solvent, in a vessel, causing evolution of a cyclopropene of formula II as a gas;

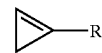

A further embodiment of the present invention is a method of purifying a cyclopropene gas prepared by reaction of an allyl compound with a non-nucleophilic strong base comprising scrubbing the cyclopropene gas in a scrubber with a reactive solvent mixture to remove residual allyl compound to give purified cyclopropene gas.

Another embodiment of the present invention is a method for encapsulating a purified cyclopropene gas comprising the steps of:
a) contacting a purified cyclopropene gas with a solution of an encapsulation agent in a vessel to give a precipitate of the encapsulated cyclopropene;
b) continuously separating the precipitate from the solution,
c) optionally washing the precipitate; and
d) rapidly drying the precipitate.

In each of these individual embodiments derived from individual steps of the continuous process, the optimum and preferred conditions are similar to those described above for the continuous process itself.

The method of this invention is illustrated by the following examples:

EXAMPLE 1

Continuous Process

Mineral oil (12.6 parts), sodium amide (12.6 parts), and hexamethyldisilazane (1 part) were added to an inerted stirred slurry hold tank. After allowing the contents of the slurry tank to blend, the resulting mixture was co-fed into an inerted heated stirred reactor along with 3-chloro-2-methylpropene ("CMP"). A heating jacket on the reactor was maintained at a temperature of 60° C. and the feeds were set to a ratio of approximately 2:3 (slurry to CMP). As the reaction proceeded the combined reaction mass overflowed through an outlet on the reactor into an adjacent hold tank. Periodically, as the tank filled, it was emptied into sufficient water to quench any remaining unreacted sodium amide and to dissolve the salt produced in the reaction.

The crude product gas stream produced in the reactor was passed through a condenser to condense some of the unreacted CMP which flowed back into the reactor. The product stream was then washed with water in a countercurrent scrubber to remove ammonia. The washing was carried out by passing the gas stream up through a glass 10 perforated tray distillation column with a stream of cooled water flowing down the column. The water flow was approximately 2–3 times the slurry feed rate into the reactor and was discarded after use. The gas was then further purified by washing in a second countercurrent scrubber with a solution of water/ethanolamine/2-mercaptoethanol/isopropyl alcohol (50:10:10:30). This operation was carried out as described for the ammonia removal except that the solution was recirculated and reused. The flow rate was 30–40 times the slurry feed rate into the reactor. Portions of the solution were removed and replaced with fresh solution throughout the washing process.

Using this procedure, the process produced approximately 31 parts of purified 1-methylcyclopropene ("1-MCP") gas per 100 parts of slurry fed into the reactor.

A stock solution of α-cyclodextrin was prepared by dissolving 1 part of technical grade α-cyclodextrin in 7.6 parts water.

The purified 1-MCP from above was encapsulated by bubbling the gas into a stirred vessel containing some of the α-cyclodextrin stock solution. Product formation was evident by the formation of a slurry of white precipitate (α-cyclodextrin/1-MCP complex). During the 1-MCP addition, fresh α-cyclodextrin solution was added to the vessel at a rate that was approximately 60 times the slurry feed rate to the reactor. The slurry of precipitated α-cyclodextrin/1-MCP complex was removed from the encapsulation vessel at a rate sufficient to maintain constant volume in the vessel.

Samples of the slurry from the encapsulation vessel were filtered using a Büchner type funnel. The resulting wetcake was allowed to air dry or in some cases was washed with solvents such as methanol or ethanol and then allowed to air dry. The levels of 1-MCP in the encapsulated product ranged from 0.5 to 2.8 percent, by weight, depending on the method of drying.

EXAMPLE 2

Alternate Product Isolation and Washing Procedure

Purified 1-MCP gas as prepared above at a flow rate of 40 g/hr was introduced continuously over a 1 hour period into an agitated 5 liter flask containing 400 g of α-cyclodextrin and 3600 g water. The solution of α-cyclodextrin turned white as precipitated α-cyclodextrin/1-MCP complex formed a slurry. This resulting slurry, as well as the wash solvents used in the following washing step, were cooled in an ice water bath to near 0° C. A portion of the chilled slurry (300 g) was filtered through a filter cloth mounted in a Büchner type filter with 100 cm² of active area, a maximum air flow rate of 20 liter/min, and open drainage at the bottom for rapid dewatering. Vacuum was used to pull the water out. This was immediately followed by pouring 60 mL of cold methanol over the filter cake as a wash, then immediately pouring 60 mL of cold methyl formate over the cake as a second wash. Using a heat gun, overhead air at 80° C. was introduced over the filter cake while the vacuum remained on, pulling the heated air through the cake as it dried. After 5 minutes, the cake was dry. Analysis showed the 1-MCP content was 4.5 percent, by weight, in the resulting powder.

EXAMPLE 3

Gas Stream Purification

A scrubbing column to remove methalyl chloride was assembled using a 10 tray 1 or 2 inch diameter perforated plate column, a scrubbing solution reservoir, a pump to transfer the scrubbing solution from the reservoir to the top of the column, and a recycle line to return the scrubbing solution from the bottom of the column to the reservoir. To the bottom of the column was charged a gas stream of crude 1-MCP. The levels of methalyl chloride in both the incoming and outgoing gas streams were measured using gas chromatography. The results are shown in the following table:

|  | CMP Levels | |
| --- | --- | --- |
| Test Solution | Incoming | Outgoing |
| 10% Sodium Hydroxide, 20% Methanol, 70% Water | 4.0% | 3.2% |
| 20% Ethanolamine, 40% Isopropyl Alcohol, 40% Water | 4.3% | 1.3% |
| 7% 1,4-Diazabicyclo[2.2.2]octane, 30% Isopropyl Alcohol, 63% Water | 4.1% | 0.2% |
| 10% Ethanolamine, 14% Mercaptoacetic acid, 38% Isopropyl Alcohol, 38% Water | 5.3% | 1.8% |
| 17% Ethanolamine, 13% Mercaptoacetic acid, 35% Isopropyl Alcohol, 35% Water | 4.8% | 0.2% |
| 10% Ethanolamine, 10% 2-Mercaptoethanol, 80% Water | 4.6% | 1.3% |
| 7% Ethanolamine, 7% 2-Mercaptoethanol, 29% Isopropyl Alcohol, 57% Water | 5.0% | <0.1% |

We claim:

1. A method of purifying a cyclopropene gas prepared by reaction of an allyl compound with a non-nucleophilic strong base comprising scrubbing the cyclopropene gas in a scrubber with a reactive solvent mixture to remove residual allyl compound to give purified cyclopropene gas.

* * * * *